United States Patent
Vedage et al.

[11] Patent Number: 5,932,769
[45] Date of Patent: Aug. 3, 1999

[54] MULTI-METALLIC ACTALYSTS FOR AMINATION OF ALCOHOLS TO FORM ALKYLAMINES

[75] Inventors: Gamini Ananda Vedage, Bethlehem; Kathryn Sue Hayes, Norristown; Malee Leeaphon, Allentown; John Nelson Armor, Orefield, all of Pa.

[73] Assignee: Air Products and Chemicals, Inc., Allentown, Pa.

[21] Appl. No.: 09/013,624

[22] Filed: Jan. 26, 1998

[51] Int. Cl.$^6$ .................................................. C07C 209/38
[52] U.S. Cl. .............................................................. 564/480
[58] Field of Search ............................................. 564/480

[56] References Cited

U.S. PATENT DOCUMENTS

| | | | |
|---|---|---|---|
| 4,683,336 | 7/1987 | Blackhurst | 564/480 |
| 4,760,190 | 7/1988 | Twigg | 564/480 |
| 4,994,620 | 2/1991 | Fong et al. | 564/473 |

*Primary Examiner*—Brian M. Burn
*Attorney, Agent, or Firm*—Mary E. Bongiorno

[57] ABSTRACT

A process for the production of aliphatic amines by reacting aliphatic alcohols with an amino compound in the presence of a catalyst containing at least two inter-dispersed metals, in a multi-metallic structure, in which at least one of the metals is nickel or cobalt, and at least one other metal is palladium, platinum, rhodium, ruthenium, or copper.

13 Claims, No Drawings

MULTI-METALLIC ACTALYSTS FOR AMINATION OF ALCOHOLS TO FORM ALKYLAMINES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Catalytic processes for the amination of aliphatic alcohols to form aliphatic amines are known. One of the most widely practiced routes is the reaction of ammonia with alcohols at relatively high operating temperatures (about 250 to 500° C.) and low to moderate pressures (atmospheric to about 200 atm) in the presence of dehydration catalysts such as aluminum oxide, silica, aluminum phosphate, or chromium oxide. Alkylation of ammonia with alcohols has also been carried out in the presence of hydrogen and a hydrogenation catalyst such as copper, nickel, cobalt and platinum. Below are described representative patents illustrating catalysts used in the amination of alcohols to produce amines:

U.S. Pat. No. 4,683,336 (Blackhurst, 1987) discloses a catalyst containing copper carbonate and nickel carbonate and/or cobalt carbonate for producing amines from the reaction of an aliphatic alcohol and/or aliphatic aldehyde with an aminating agent.

U.S. Pat. No. 4,760,190 (Twigg, 1988) discloses production of alkylamines by reacting an alcohol with an amino compound, using a catalyst containing nickel and/or cobalt and at least one metal oxide that is difficult to reduce, e.g., alumina.

U.S. Pat. No. 4,994,620 (Fong et al., 1991) discloses the alkylation of mono- and di-lower kylamines, e.g., methylamine or dimethylamine, by reacting with $C_{8-22}$ alcohol at a temperature of about 150–275° C. in the presence of hydrogen and a copper-zinc-alkaline earth metal base containing catalyst.

BRIEF SUMMARY OF THE INVENTION

This invention is directed to an improved process for producing aliphatic amines in which a multi-metallic catalyst is used in reacting an amino compound with an aliphatic alcohol. The multi-metallic catalyst is a catalyst containing interspersed metals in a composite-like structure, wherein at least one metal is nickel or cobalt and at least one other metal is palladium, platinum, rhodium, ruthenium, or copper. Catalysts having a multi-metallic structure are frequently carried on a single support such as, alumina, silica and titania. The multi-metallic catalysts of this invention provide the following advantages:

- conversion rates are significantly improved at lower metal loading compared to known amination catalysts; and
- activation of the catalysts can be carried out at lower temperatures compared to known amination catalysts.

BRIEF DESCRIPTION OF THE SEVERAL VIEWS OF THE DRAWINGS

Not applicable.

DETAILED DESCRIPTION OF THE INVENTION

The invention is directed to an improved amination process in which a catalyst having multi-metallic structure is used in producing alkylamines from amination of alcohols. By multi-metallic structure is meant a structure in which the metals are inter-dispersed with one another so as to form a type of composite.

The multi-metallic catalyst of this invention comprises nickel or cobalt in combination with palladium, platinum, rhodium, ruthenium, or copper. The catalyst contains, based on the total weight of the catalyst, from 4 to 40 wt. % of at least one metal selected from nickel and cobalt, and from 0.1 to 5 wt. % of at least one of palladium, platinum, rhodium, ruthenium, or copper; preferably 10 to 25 wt. % of nickel or cobalt, and 0.5 to 3 wt % palladium, platinum, rhodium, ruthenium, or copper.

Multi-metallic catalysts can be prepared by simultaneous precipitation of the metal salts, such as nitrate or carbonate salts, preferably, onto a single support. The catalyst is then dried and calcined to obtain the final catalyst. Calcining is typically conducted at temperatures ranging from 400 to 80° C. in air. The catalyst is then activated by heating, in air or under hydrogen, at temperatures between about 200° C. and 500° C. for about 12 hours.

The catalyst support is any of those conventionally used for these types of processes, such as alumina, silica, titania, kieselguhr, synthetic or natural zeolites, and the like. Although the supports are generally inert, they may be somewhat active so long as they do not adversely interfere with the hydrogenation process. For reasons of efficiency and economy, the preferred support is alumina.

The multi-metallic catalysts of this invention are distinguished from physical mixtures or blends by the inter-dispersion of two or more metals to form an intimate composite structure. In a physical mixture or blend, it is believed that the metals are not in close enough proximity to form a different structure as in the multi-metallic structure. In a multi-metallic structure, one metal's proximity to another can influence the electronic structure of both metals. It is believed that this change in electronic structure influences the catalytic performance of the multi-metallic catalyst.

A variety of alkyl alcohols can be aminated in the presence of the catalyst of this invention, including $C_2$ to $C_{18}$, straight chain or branched alkyl alcohols, and mixtures thereof. For example, ethanol, propanol, isopropanol, butanol, isobutanol, 1-pentanol, 1-hexanol, 2-ethyl-1-hexanol, 1-decanol, 1-dodecanol, and the like.

The amino compound in the amination of the alkyl alcohols is typically ammonia or alkylamines. The alkylamines can be linear or branched, saturated or unsaturated and have from 1 to about 18 carbon atoms, preferably 1 to 8 carbon atoms. Examples of appropriate alkylamines are: methylamine, ethylamine, propylamine, isopropylamine, butylamine, 2-ethylhexylamine, cyclohexylamine, dimethylamine, diethylamine, dioctylamine, and the like. Of course, mixtures of amines and mixtures of amines with ammonia can also be employed.

The relative amounts of alcohol in comparison to amino compound or hydrogen can vary greatly. N/R refers to the ratio of the number of moles of amino compound to the number of moles of alcohol and can vary between about 0.1/1 to 50/1; preferably 0.1/1 to 20/1. H/R refers to the ratio of the number of moles of hydrogen to the number of moles of alcohol and can vary between 0.5/1 to 50/1; preferably 0.5/1 to 10/1.

Conditions for alcohol amination can be those conventionally used in the prior art for continuous processes. For example, reaction temperatures can range from about 100 to 250° C., preferably 150 to 200 ° C. and pressures can range from 1 to 40 bar, preferably 1 to 20 bar. The gas hourly space velocity (GHSV) can range from 100 to 10,000 hr$^{-1}$; preferably 500 to 5,000 hr$^{-1}$. GHSV is the total moles of reactants per hour multiplied by 22,400 cc/mole and then divided by the amount (cc) of catalyst. The reaction is preferably conducted in the presence of hydrogen during at least a portion of the reaction.

Known liquid phase amination methods can be used. For example alcohol can be charged, under an inert gas such as nitrogen or hydrogen, to a stirred reaction vessel containing the catalyst and the ammonia or the alkylamine, and the reaction vessel heated to the desired reaction temperature.

The invention will be further clarified by a consideration of the following examples, which are intended to be purely exemplary of the invention.

EXAMPLE 1

Nickel Bimetallic Catalysts

The activity of 20% Ni/1% Pd on alumina was compared to 20% nickel on alumina, 1% palladium on alumina, and a commercial 42% nickel on alumina catalyst (HSC102B; supplied by Air Products and Chemicals, Inc.) in the amination of butanol. In order to determine the activity of the catalysts, reaction conditions were varied to achieve kinetic conversion (i.e., less than full conversion) of alcohol to amines. By maintaining other reaction conditions (i.e., pressure and flow rate), it was found that 170° C. was the temperature at which kinetic reaction conditions could be achieved and, thus, the activity of the catalyst could be accurately determined. Results are presented in Table 1 (below). The 20% nickel catalyst (20% Ni/Al$_2$O$_3$) was prepared by adding 9.9 g Ni(NO$_3$)$_2$.6H$_2$O to 15 g of de-ionized (DI) water. To this solution was added 10 g of alumina with mixing. The catalyst was dried overnight at 100° C. and calcined at 400° C. for 3 hours in air to obtain the final catalyst.

The bimetallic catalyst (20% Ni/1% Pd/Al$_2$O$_3$) was prepared by adding 9.9 g Ni(NO$_3$)$_2$.6H$_2$O to 15 g of DI water and 1.18g Pd(NO$_3$)$_2$ (8.5% Pd). Alumina (10 g) was then added to the solution and the combination was mixed well. The catalyst was dried overnight at 100° C. and calcined at 400° C. for 3 hours in air to obtain the final catalyst.

Catalysts were activated by passing 100 sccm hydrogen at 20° C. through the catalyst bed at 17 bar pressure and increasing the reactor temperature to 400° C., for 12 hours.

The reactor temperature was then reduced to 190 or 170° C. and ammonia was fed over the catalyst at 10 cc/hr for 4 hours, the hydrogen flow adjusted, and the alcohol feed flow started until the desired flow rate (GHSV) was reached.

TABLE 1

Amination of Butanol

| Catalyst | Temp, ° C. | Conversion, % | Product, % | | | GHSV*, hr$^{-1}$ | N/R/H** |
|---|---|---|---|---|---|---|---|
| | | | BuNH$_2$ | Bu$_2$NH | Bu$_3$N | | |
| 20% Ni/ Al$_2$O$_3$ | 190 | 98.9 | 31.7 | 55.8 | 12.4 | 1593 | 5.7/1/5.3 |
| | 190 | 94.9 | 38.3 | 51.1 | 10.3 | 1727 | 2.8/1/2.6 |
| | 170 | 62.0 | 70.9 | 24.6 | 4.1 | 1727 | 2.8/1/2.6 |
| 1% Pd/ Al$_2$O$_3$ | 190 | 17.6 | 48.0 | 46.8 | 5.1 | 1727 | 2.8/1/2.6 |
| | 170 | 5.6 | 51.4 | 44.3 | 4.5 | 1727 | 2.8/1/2.6 |
| 20% Ni/ 1% Pd/Al$_2$O$_3$ | 190 | 94.7 | 43.8 | 48.6 | 7.3 | 1727 | 2.8/1/2.6 |
| | 170 | 78.7 | 49.4 | 42.4 | 7.9 | 1727 | 2.8/1/2.6 |
| 42% Ni/ Al$_2$O$_3$ | 190 | 95.5 | 42.6 | 46.4 | 10.7 | 1727 | 2.8/1/2.6 |
| | 170 | 61.6 | 72.7 | 23.2 | 3.6 | 1727 | 2.8/1/2.6 |

$$*GHSV = \frac{\text{\# moles of alcohol, ammonia, and hydrogen/hr} \times 22,400 \text{ cc/mole}}{\text{cc of catalyst}}$$

**N/R/H: Mole ratio of ammonia or amine/alcohol/hydrogen.

Data for conversion at 170° C. (kinetic reaction conditions), presented in Table 1, show that the 20% nickel/ 1% palladium bimetallic catalyst was substantially more active (78.7% conversion) than 20% or 42% nickel alone (62% conversion), or 1% palladium (5.6% conversion.) The activity of the bimetallic catalyst was about 14% greater than the additive effect of 20% nickel plus 1% palladium or 42% nickel and 1% palladium. These data show that increasing the amount of nickel from 20 to 42% in the catalyst did not change the activity at kinetic reaction conditions; however, the 20% nickel/1% palladium bimetallic catalyst showed a 20% increase in activity over either 20% nickel or 42% nickel alone.

EXAMPLE 2

Cobalt Bimetallic Catalysts

Two cobalt/palladium bimetallic catalysts (each on a different support) were screened for alcohol amination and compared to three UCI (United Catalyst Incorporated) catalysts. The catalysts were tested in an isopropylamine process and in an ethylamine process. The isopropylamine process is the reaction of ammonia and isopropyl alcohol at 193° C., 250 psi (17 bar) with an ammonia to isopropanol (N/C) molar feed ratio of 4, hydrogen to alcohol (H/C) molar feed ratio of 0.8 and a GHSV of 2400 hr$^{-1}$. The ethylamine process is the reaction of ethanol and diethylamine at 164° C., 250 psi (17 bar) and 1000 hr$^{-1}$ GHSV. Table 2a and 2b give experimental conditions and Tables 3a and 3b present results of the reactions.

Each catalyst was pretreated by passing 100 sccm (standard cubic centimeters) hydrogen through the catalyst bed at 17 bar pressure and increasing the reactor temperature to either 200 or 400° C. for 12 hours, in order to activate the catalyst. The reactor temperature was then lowered and ammonia was fed over the catalyst at 10 cc/hr for 4 hours, the hydrogen flow adjusted, and the alcohol feed flow was started until the desired flow rate (GHSV) was reached.

TABLE 2a

Catalyst Composition

| Catalyst | Composition* | Activation Temperature, °C. |
|---|---|---|
| A | 14% Co/1% Pd/gamma alumina | 200 |
| B | 14% Co/1% Pd/kappa alumina | 200 |
| C | 15–20% Co/KA (kappa alumina) spheres | 400 |
| D | 15–20% Co/alumina (lot #T869) | 400 |
| E | 33% Co/$Al_2O_3$ | 400 |

*Catalysts C, D, and E were supplied by United Catalysts Inc.

TABLE 2b

Experimental Conditions

| | Isopropylamine Process | Ethylamine Process |
|---|---|---|
| Pressure | 17 bar (250 psig) | 17 bar (250 psig) |
| Temperature | 193° C. (380° F.) | 164° C. (380° F.) |
| Feedstock | Ammonia and Isopropanol | Diethylamine and Ethanol |
| Molar Feed N/R | 4 | 0.2 |
| Molar Feed H/R | 0.8 | 2.5 |
| GHSV ($h^{-1}$) | 2400 | 1000 |

N/R: Amine/Alcohol ratio
H/R: Hydrogen/Alcohol ratio

TABLE 3a

Reaction of Ammonia and Isopropyl alcohol

| Catalyst | % Conversion | MIPA, wt % | DIPA, wt % |
|---|---|---|---|
| A (14% Co/1% Pd) | 91.78 | 73.38 | 18.14 |
| B (14% Co/1% Pd) | 93.67 | 77.10 | 19.56 |
| C (15–20% Co) | 17.30 | 98.96 | 0 |
| D (15–20% Co) | 28.20 | 98.47 | 0.27 |
| E (33% Co) | 85.04 | 96.95 | 2.66 |

MIPA: monoisopropylamine
DIPA: diisopropylamine

The data in Tables 3a show that, in the isopropylamine process, the bimetallic catalysts (14% cobalt/1% palladium/ gamma or kappa alumina catalysts (A and B)) had better activity than to 33% cobalt/alumina (E) and was considerably more active than 15–20% cobalt/alumina catalysts (C and D).

TABLE 3b

Reaction of Ethanol and Diethylamine

| Catalyst | DEA Conversion, wt % | TEA/DEA Ratio |
|---|---|---|
| A (14% Co + 1% Pd) | 99.14 | 92 |
| B (14% Co + 1% Pd) | 99.73 | 116 |
| C (15–20% Co) | 66.8 | 2 |
| E (33% Co) | 99.03 | 106 |

DEA: Diethylamine
TEA: Triethylamine

In the ethylamine process (Table 3b), the data show that the 14% cobalt/1% palladium bimetallic catalysts (A and B) were similar in activity to 33% cobalt on alumina (E) and were substantially better than 15–20% cobalt alone (C).

Note also that the bimetallic cobalt catalysts can be activated at a substantially lower temperature (200° C.) compared to cobalt alone (400° C.); thus reducing the energy requirements of the process.

We claim:

1. A process for the production of the production of aliphatic amines comprising reacting aliphatic alcohols with an amino compound in the presence of a catalyst consisting essentially of two inter-dispersed metals having a multi-metallic structure wherein one of the metals is selected from the group consisting of nickel and cobalt, and the other metal is palladium.

2. The process of claim 1 wherein the amino compound is ammonia and the catalyst is carried on a single support.

3. The process of claim 2 wherein the support is selected from the group consisting of alumina, silica and titania.

4. The process of claim 3 wherein the catalyst is a bimetallic catalyst on an alumina support and consists essentially of, based on the total weight of the catalyst, from 4 to 40 wt. % of a metal selected from the group consisting of nickel and cobalt, and from 0.1 to 5 wt. % of palladium.

5. The process of claim 4 wherein the catalyst consists essentially of cobalt and palladium.

6. The process of claim 3 wherein the catalyst consists essentially of 10 to 25 wt. % nickel or cobalt, and 0.5 to 3 wt. % palladium.

7. The process of claim 3 wherein the catalyst consists essentially of 10 to 25 wt. % cobalt, and 0.5 to 3 wt. % palladium.

8. The process of claim 7 wherein the aliphatic alcohol is a $C_2$ to $C_{18}$ straight or branched chain aliphatic alcohol.

9. The process of claim 8 wherein the aliphatic alcohol is a $C_2$ to $C_4$ aliphatic alcohol.

10. A process for the production of aliphatic amines comprising reacting aliphatic alcohols with an amino compound in the presence of a catalyst consisting essentially of interspersed cobalt and palladium having a multi-metallic structure and carried on an alumina support.

11. The process of claim 10 wherein, based on the total weight of the catalyst, from 4 to 40 wt. % cobalt, and from 0.1 to 5 wt. % is palladium.

12. The process of claim 11 wherein, based on the total weight of the catalyst, from 10 to 25 wt. % is cobalt, and from 0.5 to 3 wt. % is palladium.

13. The process of claim 12 wherein the aliphatic alcohol is a $C_2$ to $C_4$ straight or branched chain aliphatic alcohol.

* * * * *

UNITED STATES PATENT AND TRADEMARK OFFICE
CERTIFICATE OF CORRECTION

PATENT NO.  : 5,932,769
DATED       : Aug. 3, 1999
INVENTOR(S) : Vedage, et al.

It is certified that error appears in the above-indentified patent and that said Letters Patent is hereby corrected as shown below:

On the title page, item [54] and column 1, line 1:
In the title
    Delete the word "ACTALYSTS" and substitute therefor -- CATALYSTS Signed and Sealed this Seventh Day of December, 1999

Attest:

Q. TODD DICKINSON

Attesting Officer

Acting Commissioner of Patents and Trademarks